(12) United States Patent
Igaki

(10) Patent No.: US 8,784,466 B2
(45) Date of Patent: Jul. 22, 2014

(54) STENT DELIVERY SYSTEM

(75) Inventor: Keiji Igaki, Kyoto (JP)

(73) Assignee: Kabushikikaisha Igaki Iryo Sekkei, Kyoto (JP)

( * ) Notice: Subject to any disclaimer, the term of this patent is extended or adjusted under 35 U.S.C. 154(b) by 906 days.

(21) Appl. No.: 10/556,993

(22) PCT Filed: May 21, 2004

(86) PCT No.: PCT/JP2004/007330
§ 371 (c)(1),
(2), (4) Date: Nov. 16, 2005

(87) PCT Pub. No.: WO2004/103450
PCT Pub. Date: Dec. 2, 2004

(65) Prior Publication Data
US 2006/0235501 A1    Oct. 19, 2006

(30) Foreign Application Priority Data
May 23, 2003  (JP) ............................. P2003-146770

(51) Int. Cl.
*A61F 2/06* (2013.01)
(52) U.S. Cl.
USPC ....................................... 623/1.11
(58) Field of Classification Search
USPC ................. 623/1.11, 1.12; 606/108, 194
See application file for complete search history.

(56) References Cited

U.S. PATENT DOCUMENTS

| | | | |
|---|---|---|---|
| 4,732,152 A * | 3/1988 | Wallsten et al. | 623/1.11 |
| 4,950,227 A * | 8/1990 | Savin et al. | 623/1.12 |
| 5,019,090 A | 5/1991 | Pinchuk | |
| 5,108,416 A * | 4/1992 | Ryan et al. | 606/194 |
| 5,456,694 A * | 10/1995 | Marin et al. | 623/1.11 |
| 5,549,635 A * | 8/1996 | Solar | 623/1.12 |
| 5,593,412 A * | 1/1997 | Martinez et al. | 623/1.11 |

(Continued)

FOREIGN PATENT DOCUMENTS

| | | |
|---|---|---|
| EP | 1033145 | 9/2000 |
| EP | 1033145 A1 * | 9/2000 |

(Continued)

OTHER PUBLICATIONS

Supplementary European Search Report mailed Aug. 24, 2011, for corresponding European Appln. No. 04734394.

*Primary Examiner* — Darwin Erezo
*Assistant Examiner* — Amy Shipley
(74) *Attorney, Agent, or Firm* — K&L Gates LLP

(57) ABSTRACT

Disclosed is an apparatus for delivery of a stent for a vessel used for implanting the stent for a vessel in the blood vessel. The delivery system includes a protective sheath (1), inserted into the vessel of a living body, a catheter (2) inserted for back-and-forth movement in the protective sheath (1), a balloon (4) arranged on the outer peripheral surface towards the distal end side of the catheter (2), configured to be protruded from the distal end of the protective sheath (1), so that the balloon is expanded by a fluid supplied to the catheter (2), and a stent for a vessel (5) formed of a biodegradable material. The stent for a vessel (5) is mounted in a state contracted in diameter on the balloon (4) and is moved back and forth along with the balloon (4) relative to the protective sheath (1). The stent for a vessel has at least one end part temporarily held by a temporary holding member (23).

20 Claims, 12 Drawing Sheets

(56) References Cited

U.S. PATENT DOCUMENTS

| | | | |
|---|---|---|---|
| 5,643,278 A * | 7/1997 | Wijay | 623/1.11 |
| 5,709,703 A | 1/1998 | Lukic et al. | |
| 5,935,135 A * | 8/1999 | Bramfitt et al. | 623/1.11 |
| 6,045,568 A | 4/2000 | Igaki et al. | |
| 6,059,813 A * | 5/2000 | Vrba et al. | 606/198 |
| 6,254,609 B1 * | 7/2001 | Vrba et al. | 606/108 |
| 6,273,895 B1 * | 8/2001 | Pinchuk et al. | 606/108 |
| 6,280,412 B1 * | 8/2001 | Pederson et al. | 604/103.07 |
| 6,331,186 B1 * | 12/2001 | Wang et al. | 623/1.11 |
| 6,395,008 B1 * | 5/2002 | Ellis et al. | 606/108 |
| 6,395,017 B1 * | 5/2002 | Dwyer et al. | 623/1.11 |
| 6,432,129 B2 * | 8/2002 | DiCaprio | 623/1.11 |
| 6,478,814 B2 * | 11/2002 | Wang et al. | 623/1.12 |
| 6,500,204 B1 | 12/2002 | Igaki | |
| 6,562,063 B1 * | 5/2003 | Euteneuer et al. | 623/1.12 |
| 6,645,239 B1 | 11/2003 | Park et al. | |
| 6,660,031 B2 * | 12/2003 | Tran et al. | 623/1.12 |
| 6,740,113 B2 * | 5/2004 | Vrba | 623/1.12 |
| 6,858,034 B1 * | 2/2005 | Hijlkema et al. | 606/108 |
| 6,899,727 B2 * | 5/2005 | Armstrong et al. | 623/1.12 |
| 7,338,518 B2 * | 3/2008 | Chobotov | 623/1.12 |
| 7,393,358 B2 * | 7/2008 | Malewicz | 623/1.11 |
| 7,473,271 B2 * | 1/2009 | Gunderson | 623/1.12 |
| 7,632,298 B2 * | 12/2009 | Hijlkema et al. | 623/1.12 |
| 7,717,949 B2 * | 5/2010 | Dorn | 623/1.11 |
| 8,066,754 B2 * | 11/2011 | Malewicz | 623/1.11 |
| 8,439,961 B2 * | 5/2013 | Jagger et al. | 623/1.11 |
| 2002/0055767 A1 * | 5/2002 | Forde et al. | 623/1.11 |
| 2002/0072789 A1 * | 6/2002 | Hackett et al. | 623/1.12 |
| 2002/0099405 A1 | 7/2002 | Yurek et al. | |
| 2002/0120322 A1 | 8/2002 | Thompson et al. | |
| 2002/0183827 A1 * | 12/2002 | Derus et al. | 623/1.12 |
| 2003/0074044 A1 * | 4/2003 | Randby et al. | 623/1.11 |
| 2004/0049204 A1 * | 3/2004 | Harari et al. | 606/108 |
| 2005/0038495 A1 * | 2/2005 | Greenan | 623/1.11 |
| 2008/0161902 A1 * | 7/2008 | Poulsen | 623/1.11 |

FOREIGN PATENT DOCUMENTS

| | | |
|---|---|---|
| JP | 2068052 | 3/1990 |
| JP | 09-140804 | 6/1997 |
| JP | 2003-500105 | 1/2003 |
| WO | WO 00/13737 | 3/2000 |
| WO | WO 01/12256 | 2/2001 |
| WO | 01/34219 A2 | 5/2001 |
| WO | 02/22053 A2 | 3/2002 |

* cited by examiner

STENT DELIVERY SYSTEM

CROSS-REFERENCE TO RELATED APPLICATIONS

This application is a 371 of PCT/JP04/07330 filed May 21, 2004; which claims benefits of the JP Patent Application 2003-146770 May 23, 2003, which is incorporated by reference herein.

TECHNICAL FIELD

This invention relates to a stent delivery system used for delivering a stent for a vessel, implanted in a vessel of a living body, such as blood vessel, trachea, bile duct or urethra, for providing a support for the lumen of the vessel from the inside, to a target site for implantation in the vessel.

BACKGROUND ART

If stenosis has occurred in a vessel of a living body, such as blood vessel, a balloon forming portion provided in the vicinity of the distal end of a balloon catheter is inserted into this stenosis portion. This balloon forming portion is dilated to expand the stenosis portion of the blood vessel to improve the blood flow. This operation, known as percutaneous angioplasty (PTA), has so far been in widespread use.

However, after application of PTA to the site of occurrence of stenosis in a blood vessel, acute occlusion, attributable to the dissection of the intima, or re-narrowing of the same site as that where narrowing in the blood vessel (stenosis) has occurred, that is, re-stenosis, tends to be produced in a well-known manner at a high probability.

For preventing such acute occlusion or re-stenosis, the technique of implanting a tubular stent at the target site where PTA has been applied, has so far been used. A stent, used for the purpose, is implanted into the blood vessel, as it is contracted in diameter, and subsequently enlarged in diameter so as to be implanted in the blood vessel to support the blood vessel wall from its inside.

For a stent implanted in the blood vessel, a stent made of metal has so far been used. The metal stent is classified into a balloon expanding stent and a self-expanding stent.

The balloon expanding stent is inserted into a targeted site for implantation in the blood vessel, in a state contracted in diameter, and subsequently enlarged in diameter with expansion of the balloon. Among the stents of this type, there are a stent comprised of a small-diameter tube of stainless steel provided with numerous incisions formed by e.g. a laser cutter to permit the tube to be enlarged in diameter, and a stent formed by braiding a fine metal filament into a tube, as disclosed in U.S. Pat. No. 4,950,227.

The self-expanded stent is contracted in diameter under application of an external pressure and inserted in this contracted state in the target site for implantation in the blood vessel. After removal of the external pressure, the stent is self-expanded in diameter to support the blood vessel from its inner wall surface. As typical of this type of the self-expanded stent, there is known such a one obtained by spirally winding a fine metal wire to form a tube, as disclosed in the Japanese Laid-Open Patent Publication Hei-2-68052.

For implanting the above-described stent for a vessel in the target site in the blood vessel of a living body, a stent delivery system is used. The stent delivery system is of variable configurations, depending on the type of the stent to be delivered, that is, on whether the stent delivered is the balloon expanding stent or the self-expanded stent.

The stent delivery system for delivering the balloon expanding stent within the blood vessel includes a catheter inserted into the blood vessel, and a balloon is provided, as it is contracted in diameter, to the distal end of the catheter. On this balloon is mounted a stent as it is contracted in diameter. The stent, mounted on the balloon, is pressed from its outer peripheral side and retained against detachment from the balloon. The stent, thus mounted on the balloon, is delivered as far as the targeted site for implantation in the blood vessel, along with the balloon, by progressively inserting the catheter into the blood vessel. The stent, thus delivered to the target site for implantation in the blood vessel, is expanded in diameter on plastic deformation caused by balloon expansion to support the blood vessel wall from its inner side.

For the stent delivery system, used for implanting the balloon expanding stent in the blood vessel, it is basically only sufficient to include a means for mounting a stent, contracted in diameter, on the balloon provided to the catheter.

As the stent delivery system for delivery of the balloon expanding stent, there has been proposed such a system including a sheath covering up the stent mounted on the balloon. The sheath used is provided for preventing the stent, mounted on the balloon, from becoming detached from the balloon.

On the other hand, the stent delivery system for delivery of the balloon expanding stent into the blood vessel is constructed so that a catheter mounting a stent contracted in diameter is inserted into a protective sheath. The stent, mounted in the state contracted in diameter in the catheter, is covered up by the protective sheath and thereby maintained in the state contracted in diameter. For implanting the stent in the target site for implantation, using the above-described stent delivery system, the catheter, mounting the stent, is inserted up to the target site for implantation in the blood vessel, along with the protective sheath. At this time, the catheter is fixed and only the protective sheath is retreated in the blood vessel, whereby the stent, mounted to the distal end of the catheter, is freed from the sheath. The stent, thus freed from the protective sheath, is self-expanded by elasticity proper to the stent itself, and is dilated in diameter to a size capable of providing a support for the inner wall of the blood vessel.

The stent delivery system, used for implanting the self-expanding stent in the blood vessel, includes a catheter on which is mounted a stent, contracted in diameter, and a protective sheath in which is housed the catheter, the stent has been mounted to, there being no necessity to provide a balloon for expanding the stent.

Currently, there has not been established a method for treatment for an instance where re-stenosis has occurred on a site where angioplasty has been applied and a metal stent has been implanted.

Moreover, if metal, inherently a foreign substance for the living body, is caused to remain for a prolonged time in the living body, there is a cause that the blood vessel may thereby be affected, such as by excessive intimal hyperplasia occurring in the stent implant portion.

With a view to obviating the problems inherent in the conventional metal stent, the present Assignee has already proposed a stent formed using a biodegradable polymer (see U.S. Pat. Nos. 6,045,568, 2,842,943 and WO00/13737).

The stent formed of the biodegradable polymer may be absorbed in the tissue of the blood vessel after a preset time, has passed after it is implanted in the blood vessel, for example, after lapse of 6 to 12 months, such that the function of providing a support for the blood vessel from the inner side thereof is no longer needed. Since the stent of this type may be absorbed in vivo, it becomes possible to suppress adverse effects which might be produced as a result of the stent, as a foreign material for the living body, being left over for a prolonged time.

In particular, the present Assignee has already proposed a stent for a vessel, formed by braiding a yarn of a biodegradable polymer into a tube (U.S. Pat. No. 6,045,568), a stent for a vessel prepared by forming a yarn of a biodegradable polymer in a non-woven non-braided state (U.S. Pat. No. 2,842,943) and a stent for a vessel prepared by bending a yarn of biodegradable polymer in a zigzag design to form concatenated vee shapes, and by winding the resulting zig-zag shaped yarn into a tube, with the stent for a vessel being expanded or contracted in diameter with vee shaped portions of the yarn as portions subjected to displacements (WO00/13737). These stents were actually implanted in living bodies.

The stent formed of the biodegradable polymer is formed into a tube and subsequently heat-set, by way of heat treatment, for shape retention to a desired outer diameter. This heat-setting is carried out at a temperature not lower than the glass transition temperature and not higher than the melting point of the biodegradable polymer making up the stent. The stent which is to be implanted in the blood vessel, and which has its shape retained to a desired outer diameter, is contracted in diameter for insertion into the blood vessel. This contraction of the stent is carried out under application of an external pressure with or without heat setting. The heat-setting here is carried out at a temperature lower than the temperature for heat setting carried out for retention of the expanded state.

The stent made of the biodegradable polymer is expanded by a balloon expansion method employing a balloon. This method is carried out for promptly expanding the stent, inserted in a state contracted in diameter as far as the site for implantation in the blood vessel, to a size capable of reliably supporting the inner wall of the blood vessel.

Meanwhile, the stent, formed using the biodegradable polymer, may be warmed and thereby given the self-expanding properties, that is, the properties of shape memory. When mounted on the catheter and inserted in this state into the blood vessel of the living body, the stent, formed of the biodegradable polymer, is self-expanded, as it is warmed by body temperature of the living body. Since the stent has the self-expanding properties, it is tightly contacted with the inner wall of the blood vessel to maintain the force of dilating the blood vessel from its inside, and hence is able to distend the blood vessel from its inner wall over a preset time period until the time of biodegradation.

Thus, the stent formed of the biodegradable polymer has the self-expanding properties, even though it necessitates expansion by the balloon. For inserting this sort of the stent into the blood vessel of the living body for implantation therein, there is needed, along with the balloon for expanding the stent, an expansion inhibiting member for inhibiting self-expansion of the stent which is otherwise caused when the stent is warmed up by body temperature on insertion thereof into the blood vessel. That is, for preventing the occurrence of an accident in which the stent contracted in diameter is self-expanded on being inserted into the blood vessel and is disengaged from the balloon, it becomes necessary to provide a protective sheath to control the self-expansion of the stent mounted to the balloon.

There is also the possibility that the stent of the biodegradable polymer, exhibiting the self-expanding properties, is jumped up from the protective sheath by its force of expansion and becomes disengaged from the catheter, when the stent, delivered to the targeted site for implantation in the blood vessel of the living body, is subsequently gradually freed of the support from the protective sheath, such that a given portion of the stent is protruded from the protective sheath. The result is that not only the stent cannot be implanted in the targeted site for implantation in the blood vessel but also the stent becomes unable to be expanded by the balloon.

DISCLOSURE OF THE INVENTION

It is an object of the present invention to provide a stent delivery system whereby a stent for a vessel, formed of a biodegradable polymer and afforded with the self-expanding properties, may correctly be implanted in a target site in the vessel.

It is another object of the present invention to provide a stent delivery system whereby a stent for a vessel, which is formed of the biodegradable polymer and given the self-expanding properties, but which is furthermore in need of expansion by a balloon, may be enlarged in diameter such as to provide a reliable support for the inner wall of the vessel.

It is a further object of the present invention to provide a stent delivery system in which the location of insertion of the stent relative to the vessel may be detected from outside the living body.

It is a further object of the present invention to provide a stent delivery system whereby a stent for a vessel, mounted on the balloon, provided to the catheter, may readily be delivered to a targeted site for implantation in the vessel.

It is yet another object of the present invention to provide a stent delivery system whereby a stent for a vessel may be delivered without falling off within a small vessel which may be bent, sinuous or hardened.

For accomplishing the above object, a stent delivery system, proposed by the present invention, comprises a protective sheath inserted into a vessel of a living body, a catheter inserted into the protective sheath for performing a back-and-forth movement therein, a balloon arranged on an outer peripheral surface towards the distal end of the catheter protruded from the distal end of the protective sheath, and a stent for a vessel, formed of a biodegradable polymer. The balloon may be expanded with a fluid supplied to the catheter. The stent for a vessel is mounted in a state contracted in diameter on the balloon and is moved back and forth along with the balloon relative to the protective sheath. At least one end of the stent is retained by a temporary holding member.

The temporary holding member temporarily holds one end side, located towards the proximal side of the protective sheath, of the stent for a vessel, housed within the protective sheath. That is, the one end side, located towards the proximal side of the protective sheath, of the stent for a vessel, opposite to the side of the stent for a vessel protruded from the distal end of the protective sheath, is retained by the temporary holding member.

When freed from the retention by the protective sheath, the stent for a vessel, mounted on the balloon, has its one end side towards the proximal side of the protective sheath retained by the temporary holding member, and hence is not jumped up precipitously under the force of expansion.

Preferably, the temporary holding member, retaining the stent for a vessel, is formed as a tube of an inner diameter smaller than the outer diameter of the catheter.

The temporary holding member may hold only a part of the outer periphery of the stent for a vessel.

Preferably, the temporary holding member is formed of an elastic material to a tubular shape and retains the outer peripheral surface of the catheter as far as the one end of the stent for a vessel. At this time, the temporary holding member preferably has at least a portion thereof towards the catheter side bonded to the catheter.

The stent for a vessel, employed in the present invention, is formed of a biodegradable polymer to a tubular shape. This stent for a vessel is provided with the self-expanding function.

According to the present invention, a stent for a vessel, formed from a yarn of a biodegradable polymer to a tubular structure, and provided with the self-expanding function, is used. The stent for a vessel, formed of a biodegradable polymer, wound to a tube as the yarn is bent in a zigzag design, and expanded or contracted in diameter with the bends of the yarn as displacing portions, is used.

The protective sheath preferably is formed of a material prohibited from extension/contraction along its longitudinal direction in order to render the protective sheath scarcely extensible along the longitudinal direction.

The protective sheath has its distal end side towards a side for insertion into a vessel of a living body curved to conform to the shape of the vessel.

The protective sheath includes on its distal end side for insertion into the vessel of the living body a flexible tubular section superior in flexibility to its proximal end side.

The protective sheath includes on the distal end side for insertion into the vessel of the living body an insertion protecting part formed of a material exhibiting superior flexibility.

The protective sheath includes a radiopaque section, containing a radiopaque material, on its distal end side from which is protruded the stent for a vessel mounted on the catheter.

The catheter inserted into the protective sheath includes a radiopaque section indicating the mounting position of the stent for a vessel.

Since the radiopaque section containing a radiopaque material is provided on the distal end side of the protective sheath, and the catheter inserted into the protective sheath includes a radiopaque section indicating the mounting position of the stent for a vessel, the relative positions of the radiopaque section on the protective sheath side and the radiopaque section on the catheter may be confirmed, when the protective sheath is moved relative to the stent for a vessel, whereby it is possible to determine the positions of the catheter and the stent for a vessel relative to the protective sheath.

Other objects and specified advantages of the present invention will become more apparent from the following explanation of present embodiments of the invention which will now be made hereinbelow by referring to the drawings.

BEST MODE FOR CARRYING OUT THE INVENTION

Figure 1:
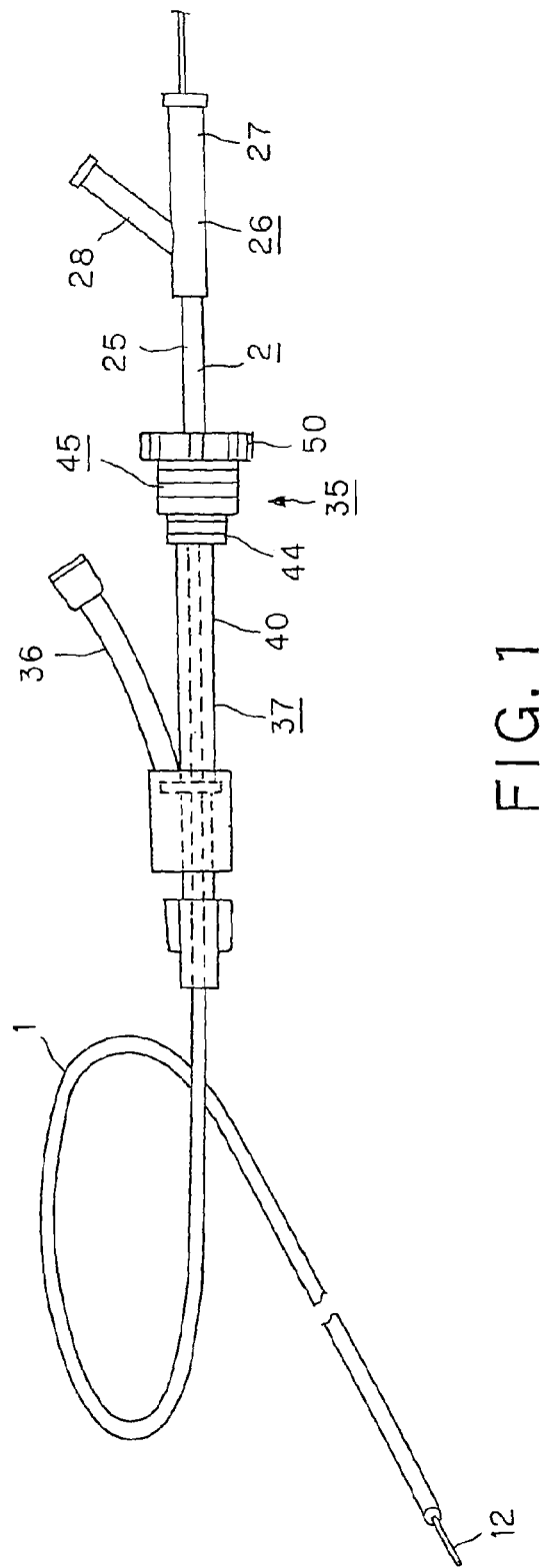
FIG. 1 is a perspective view showing a system for delivery of a stent for a vessel according to the present invention.

Referring to the drawings, present embodiments of the present invention will be explained in detail.

The stent delivery system according to the present invention is used for delivering a stent, implanted in a vessel, such as blood vessel, trachea, bile duct or urethra of a living body, for supporting the lumen of the vessel from its inner side for maintaining a patency state of the lumen, to a target site for implantation in the vessel.

In the embodiment, as now explained, the present invention is applied to a system for delivery in the blood vessel of a stent for a vascular vessel to be implanted within the blood vessel of the living body.

The stent delivery system, embodying the present invention, includes a protective sheath 1, inserted into the vessel, such as a blood vessel, of a living body, and a catheter 2, inserted into the protective sheath 1 and inserted along with the protective sheath 1 into the blood vessel, as shown in FIG. 1.

The protective sheath 1 is formed as a long flexible tube so that it may be smoothly inserted to conform to the shape e.g. of the blood vessel of the living body. The protective sheath 1 is of an outer diameter $R_1$ of approximately 2 mm to 3 mm and of a length approximately 100 cm, as shown in FIG. 2.

Figure 2:
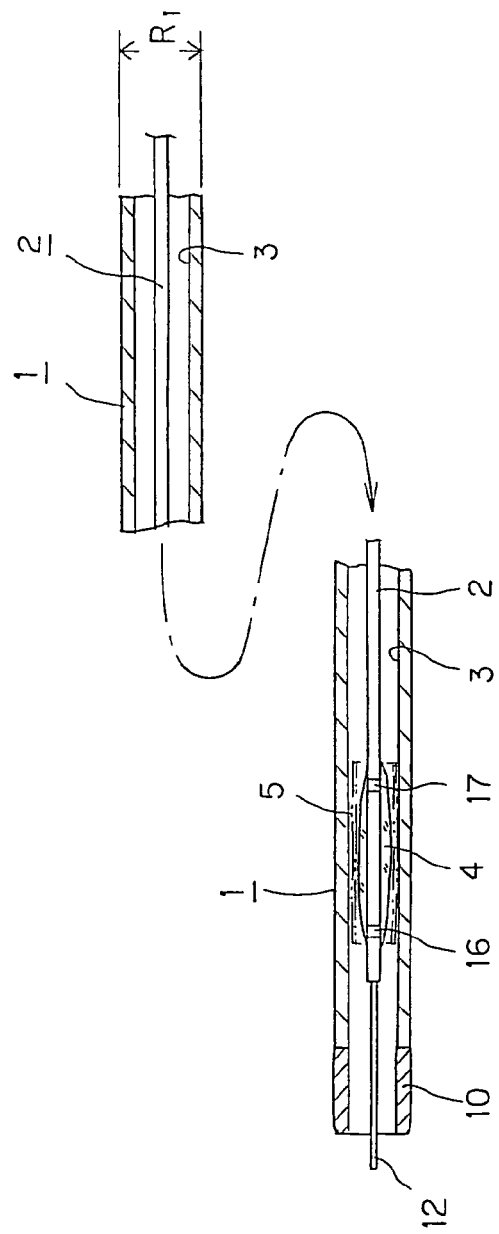
FIG. 2 is a partial cross-sectional view showing the state in which a catheter carrying the stent for a vessel has been inserted into a protective sheath.

In an inner bore opening 3 formed of the protective sheath 1, the catheter 2 is inserted so as to be reciprocated therein as shown in FIG. 2. The distal end of the catheter 2 carries a balloon 4 on which is mounted a vascular stent 5.

Meanwhile, the protective sheath 1, used for the stent delivery system, according to the present invention, is movable relative to the catheter 2, so as to assume a state in which the vascular stent 5, mounted to the distal end of the catheter 2, is housed within the protective sheath 1, and a state in which the stent is protruded outwards from the distal end. For reliably varying the position of the vascular stent 5 relative to the protective sheath 1, the length of the protective sheath 1, pulled out from the catheter 2, is accurately coincident with the length of the protective sheath 1 moved relative to the catheter 2. In addition, the protective sheath 1 is inserted into the inside of the blood vessel as the sheath is in contact with the inner wall of the blood vessel.

Hence, the protective sheath 1 is preferably formed of a material the extension and contraction of which along the long axis of the sheath are controlled to render the sheath difficultly extensible along the long axis. It is also desirable that the protective sheath 1 may be inserted smoothly as it is deformed after the shape of the blood vessel of the living body and, in addition, the catheter 2 inserted into the inner bore opening 3 may smoothly be reciprocated without any significant frictional resistance with respect to the protective sheath.

Figure 3:
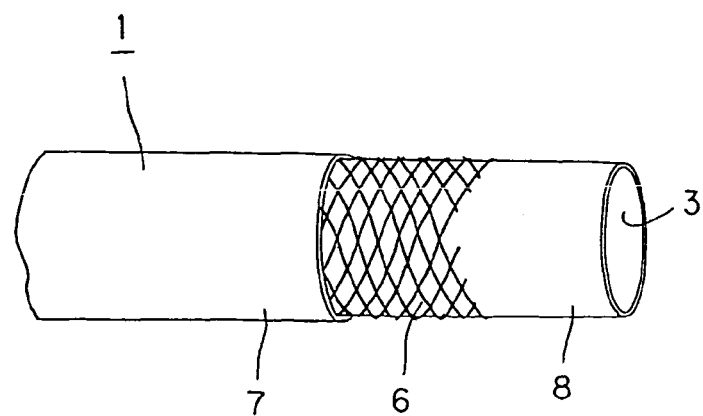
FIG. 3 is a partial perspective view showing the structure of a protective sheath.

Thus, the protective sheath 1, used in the present invention, is constructed and arranged as shown for example in FIG. 3. This protective sheath 1 is formed by a readily flexible tubular member 6 formed by braiding fine wires of e.g. stainless steel in a meshed pattern, and outer and inner coating layers 7, 8 of synthetic polymer applied to the outer and inner peripheral surfaces of the tubular member 6, thereby suppressing the sheath from performing extension or contraction along its long axis. That is, the meshed tubular member 6, coated by the outer and inner coating layers 7, 8 of synthetic polymer, is prevented from performing extension or contraction along its longitudinal direction.

The outer coating layer 7 of the protective sheath 1, contacted with the inner wall of the blood vessel when the protective sheath is inserted into the inside of the blood vessel, is preferably formed of a highly anti-hygroscopic material, for example, a polyamide-based synthetic material. On the other hand, the inner coating layer 8, having a sliding contact with the catheter 2, is preferably formed of a synthetic polymer material, low in friction and hence superior in lubricity, for example, polytetrafluoroethylene.

Figure 4:
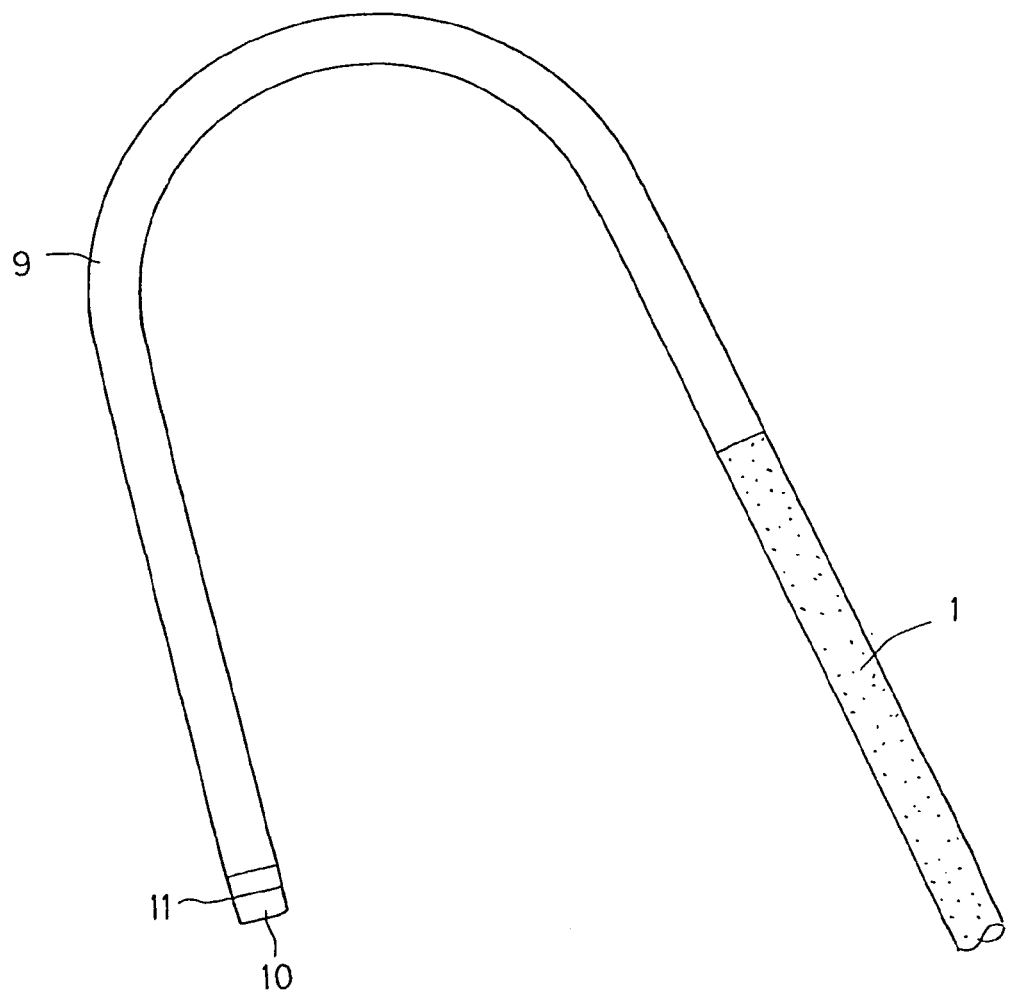
FIG. 4 is a partial perspective view showing a distal end part of the protective sheath.

Moreover, the distal end of the protective sheath 1 of the stent delivery system of the present invention, operating as an inserting end into the blood vessel of the living body, is formed as a flexible tubular part 9 exhibiting higher flexibility than its proximal side end, as shown in FIG. 4. The outer coating layer 7 of the flexible tubular part 9 is formed of a flexible and flaccid material. The protective sheath 1, the distal end of which is formed by the flexible tubular part 9, exhibiting flexibility superior to that of the main sheath body part, may readily be inserted into the blood vessel to conform to its curved profile.

Referring to FIG. 4, the flexible tubular part 9 is curved or sinuous to conform to the shape of the blood vessel, for example, artery, into which the protective sheath 1 is inserted along with the catheter 2. Since the flexible tubular part 9 at the distal end side of the protective sheath is sinuous in this manner, the protective sheath may be smoothly inserted without excessively loading the artery curved strongly to e.g. a U-shape.

At the distal end of the protective sheath 1, there is provided an insertion protecting part 10, formed of a material having superior flexibility, such as silicone rubber, as shown in FIG. 4. Since the distal end of the protective sheath 1, along the direction of insertion of the sheath into the blood vessel, is provided with the insertion protecting part 10, described above, it becomes possible to insert the protective sheath into the blood vessel with the least risk of damage to the vessel wall.

The insertion protecting part 10, provided to the distal end towards the inserting side of the protective sheath 1 into the blood vessel, is provided with a radiopaque section 11 containing a radiopaque material. By providing the radiopaque section 11 to the distal end towards the inserting side of the protective sheath 1 into the blood vessel of the living body, the position of insertion of the protective sheath into the blood vessel may be visually determined by illumination of X-rays when the protective sheath is inserted into the blood vessel, while it may also be checked whether or not the stent as well as the catheter has been protruded accurately to outside the protective sheath at the time of implanting the stent.

The radiopaque section 11 may also be provided to the distal end of the protective sheath 1 per se.

The catheter 2, the vascular stent 5 is mounted to, and which is inserted into the protective sheath 1, is formed of a synthetic polymer material, such as polyethylene, for imparting flexibility to the catheter. Since the catheter 2 is used for causing reciprocating movement of the vascular stent 5, mounted on the balloon 4, provided towards the distal end of the catheter, between the position in which the stent is housed within the protective sheath 1 and the position in which the vascular stent 5 is protruded from the protective sheath 1, the catheter 2 has an overall length larger than the protective sheath 1 by a length at least corresponding to the length of reciprocation of the vascular stent 5 plus a length of a finger support to be gripped by a user's finger when causing the reciprocating movement of the vascular stent.

Figure 5:
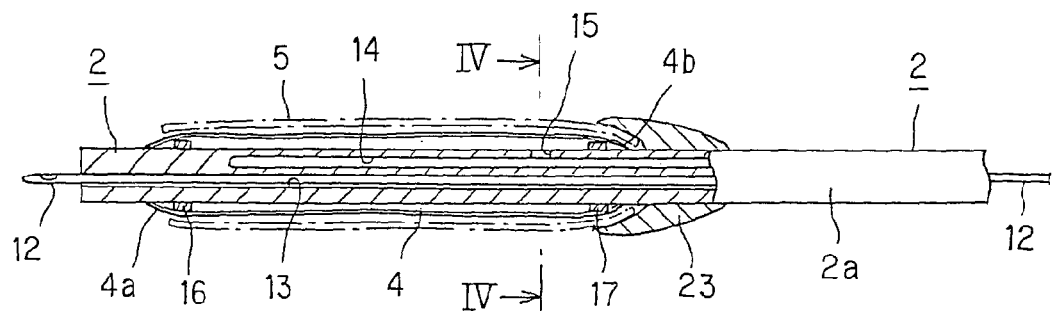
FIG. 5 is a cross-sectional view showing the state in which the stent for a vessel has been mounted on a balloon provided to the catheter.
Figure 6:
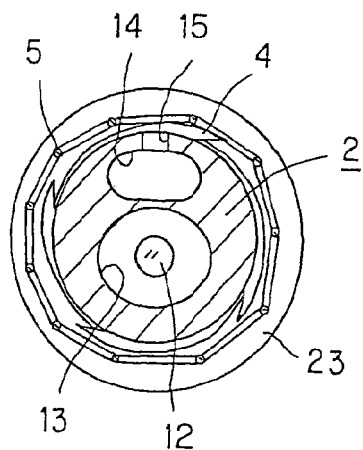
FIG. 6 is a cross-sectional view taken along line IV-IV of FIG. 5.

Referring to FIGS. 5 and 6, the catheter 2 is provided with an inner bore opening 13 for a guide wire 12 and with a fluid passage 14 for supply of a fluid, such as a contrast agent, used for expanding the balloon 4 provided to the distal end of the catheter 2. The guide wire 12 is used for guiding the catheter 2 along with the protective sheath 1 into and through the blood vessel. Meanwhile, the inner bore opening 13 for the guide wire is formed as a through-opening from the proximal end up to the distal end of the catheter 2, whilst the fluid passage 14 is formed as a blind hole and terminated short of the distal end of the catheter 2, as shown in FIG. 5.

To the distal end of the catheter 2 is mounted the balloon 4 for expanding the vascular stent 5, mounted to the catheter 2, as shown in FIG. 5. The balloon 4 is formed to a tubular shape from e.g. polyethylene (PE), polyolefinic coployner (POC) or polyethylene terephthalate (PET). The balloon 4 is mounted to cover up the outer peripheral surface on the distal end of the catheter 2, and bonded at its both ends 4a, 4b thereto, using e.g. an adhesive, so as to be unified as one with the catheter 2. In an initial state in which the balloon has been mounted to the catheter 2, the balloon 4 is collapsed and folded on its outer peripheral surface.

In the part of the catheter, the balloon 4 is mounted to, there is provided a through-hole 15 by means of which the balloon is to communicate with the fluid passage 14, as shown in FIG. 5. The contrast agent, supplied via the fluid passage 14, is charged into the inside of the balloon 4 via the through-hole 15 to expand the balloon 4. In the part of the catheter 2, the balloon 4 is mounted to, there are also formed radiopaque sections 16, 17 formed of a radiopaque material. These radiopaque sections 16, 17 are provided by mounting fine wires of metal, as a radiopaque material, to the outer peripheral surface of the catheter 2. The radiopaque sections 16, 17, provided to the catheter 2, are provided in the vicinity of both ends 4a, 4b of the balloon 4. By these radiopaque sections 16, 17, the position of insertion into the blood vessel of the vascular stent 5, mounted on the balloon 4, may be confirmed from outside the living body.

On the balloon 4, mounted to the catheter 2, there is mounted the vascular stent 5 implanted in the blood vessel of the living body using the stent delivery system according to the present invention.

The vascular stent 5, used with the stent delivery system according to the present invention, is formed of a biodegradable polymer material into a tubular form, and has a self-expanding function. A specified example of the vascular stent 5 is formed as shown in FIG. 7.

Figure 7:
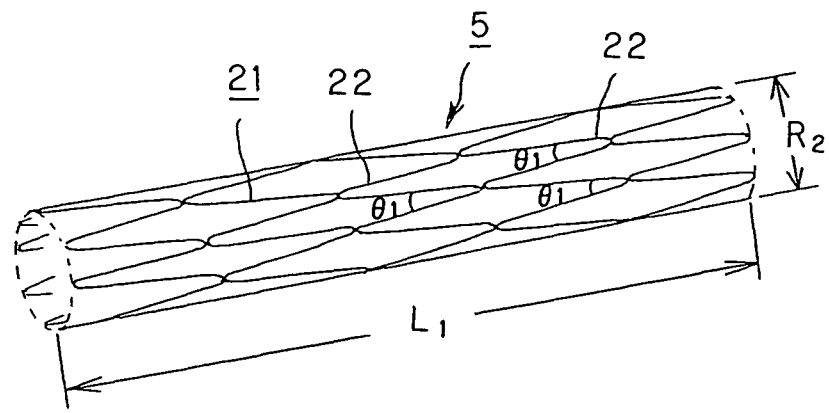
FIG. 7 is a perspective view showing an instance of the stent for a vessel used in the present invention.

The vascular stent 5, shown in FIG. 7, is formed to a tubular shape, with a yarn 21 of a biodegradable polymer. That is, this vascular stent 5 is prepared to a tubular form, in particular a cylindrical form, by bending the yarn 21 of the biodegradable polymer in a zigzag pattern to form concatenated vee shapes and by spirally winding the resulting zigzag shaped yarn into a tube, in particular a cylinder, as shown in FIG. 7.

The biodegradable polymer, forming the yarn 21, may be exemplified by aliphatic polyesters, fatty acid anhydrides, aliphatic polycarbonates, polyphosphasen and copolymers containing at least one of these substances.

Specifically, the biodegradable polymer may be one or more of such materials as poly-L-lactic acid (PLLA), polyglycolic acid, plyglactin, polydioxanone, polyglyconate, $\epsilon$-caprolactam, polylactic acid-$\epsilon$-caprolacton copolymers and polyglycolic acid-$\epsilon$-caprolacton copolymers.

The vascular stent 5, implanted in the blood vessel using the stent delivery system of the present invention, is mounted on the balloon 4, mounted on the catheter 2 in a state contracted in diameter, as shown in FIG. 5. At this time, the balloon 4 is not expanded and is in a folded state, as shown in FIG. 6. The part of the catheter 2, mounting the balloon 4, is formed to have an outer diameter approximately equal to or slightly larger than the inner diameter of the vascular stent 5, contracted in diameter, in order that the vascular stent 5, thus contracted in diameter, will be mounted on the balloon 4 in close contact therewith.

The vascular stent 5 is mounted in this manner in close contacted state on the balloon 4, mounted on the catheter 2, so that, when the balloon 4 is expanded, the vascular stent may be expanded quickly to follow up with the expansion of the balloon 4.

The vascular stent 5, mounted on the balloon 4, is inserted, along with the catheter 2, carrying the balloon 4, in the inner bore opening 3 of the protective sheath 1 for the catheter 2, and is kept in a state contracted in diameter by the protective sheath 1, as shown in FIG. 2. The vascular stent 5, inserted into the inner bore opening 3 of the protective sheath 1 for the catheter 2, transitions from the state in which the stent is mounted on the balloon 4 and housed within the protective sheath 1 to the state in which it is protruded from the distal end of the protective sheath 1, by causing movement of the protective sheath 1 relative to the catheter 2.

Meanwhile, the vascular stent 5, formed using the yarn 21, formed of the biodegradable polymer, is given the self-expanding properties, and hence the force of expansion in a direction of dilation is conferred to the stent, by the stent being inserted into the blood vessel and warmed by body temperature of the living body, without the force of expansion being applied from outside. That is, although the vascular stent 5, held by the protective sheath 1, is kept contracted in diameter, the force of expansion is stored in the stent heated by being warmed up with the body temperature.

The vascular stent 5, in which the force of expansion is stored in the protective sheath 1, is gradually freed from the support by the protective sheath 1, such that, when a part of the stent is protruded from the protective sheath 1, it is jumped up from within the protective sheath 1, and is dislocated from the catheter 2. Hence, it becomes difficult to locate the stent accurately in the targeted site for implantation within the blood vessel. Additionally, the position of the stent mounted on the balloon 4 can scarcely be maintained.

Figure 8:
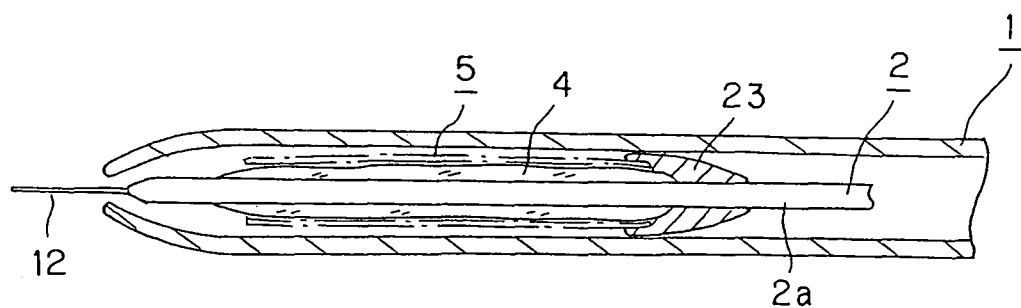
FIG. 8 is a cross-sectional side view showing the state in which the stent for a vessel, mounted on the catheter, is held by a temporary holding member.

Thus, with the vascular stent 5, used for the stent delivery system according to the present invention, has its one end retained by a temporary holding member 23, in order to prevent the stent 5 from being expanded and jumped up from the protective sheath, as shown in FIGS. 5 and 8. That is, as the vascular stent 5 is housed and held in the protective sheath 1, the one proximal side end of the stent located opposite to the distal end of the protective sheath 1, operating as an end for protrusion, is held by the temporary holding member 23.

The temporary holding member 23, temporarily holding the vascular stent 5, is formed as a tubular member covering up and temporarily holding the outer rim portion of the one end of the vascular stent 5, as shown in FIGS. 5 and 8. The temporary holding member 23 is formed of an elastic material, such as latex.

When formed of an elastic material, the temporary holding member 23 is preferably formed to a tubular shape of a diameter smaller than the outer diameter of the catheter 2. When formed to this shape, the temporary holding member 23 pressures and holds the one end of the vascular stent 5 from the outer rim portion thereof to reliably hold the vascular stent 5. The temporary holding member 23 preferably covers up the one end side of the vascular stent 5 mounted on the balloon 4 from the outer peripheral surface 2a of the catheter 2, as shown in FIGS. 5 and 8.

By the tubular temporary holding member 23 holding the vascular stent 5, the protective sheath 1 may be moved smoothly relative to the vascular stent 5, because the vascular stent 5 is held by the temporary holding member 23 and thereby maintained in a state contracted in diameter.

Figure 9:
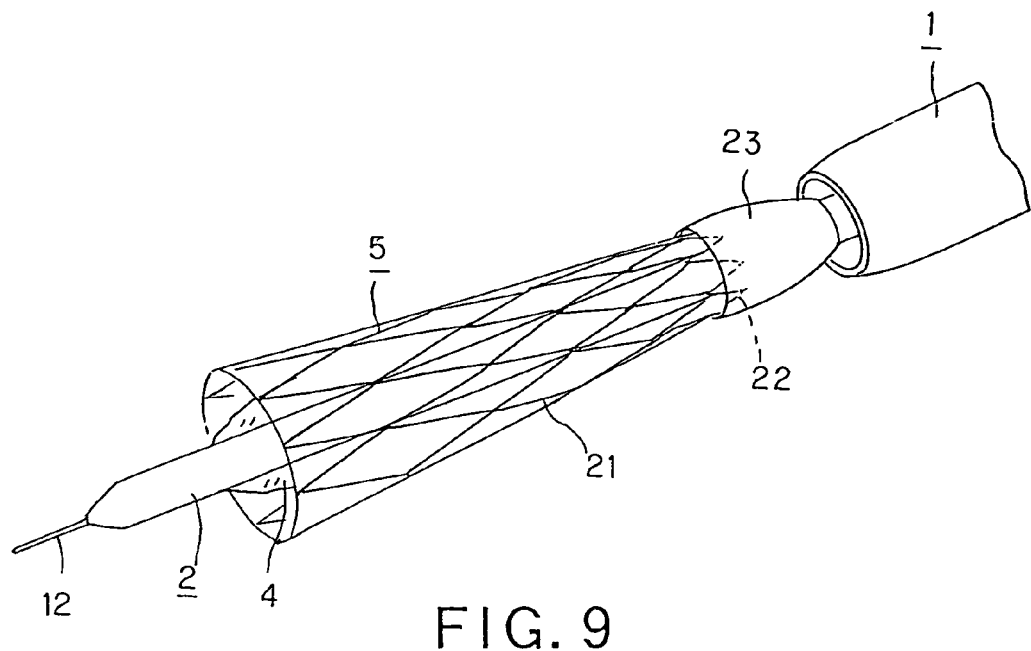
FIG. 9 is a perspective view showing the state in which the stent for a vessel, mounted on the catheter, is protruded from the protective sheath.
Figure 10:
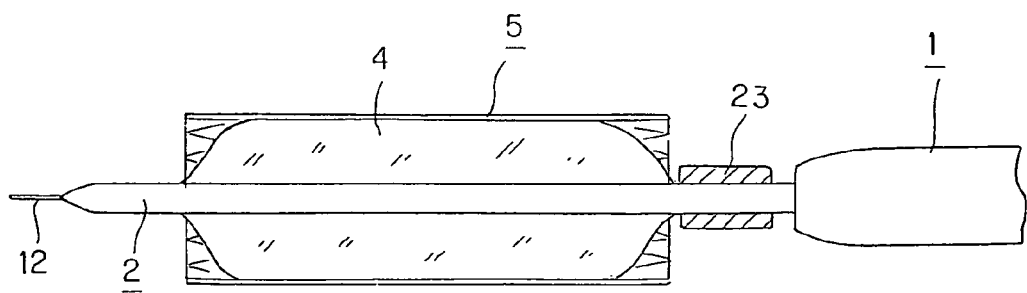
FIG. 10 is a side view showing the state in which the balloon is expanded to enlarge the diameter of the stent for a vessel.

With the vascular stent 5, having its one end held by the temporary holding member 23, the force of expansion is accumulated as long as the vascular stent is housed within the protective sheath 1, as shown in FIG. 8. When the stent is subsequently protruded from the protective sheath 1, the opposite end side of the stent, protruded initially from the protective sheath 1, is expanded under the force of expansion, accumulated therein, as shown in FIG. 9. However, the proximal one end side of the vascular stent 5 towards the proximal end of the protective sheath 1 continues to be retained by the temporary holding member 23 and is kept in the state of close contact with the balloon 4. That is, it is not the vascular stent 5 in its entirety, i.e. the stent body from its one end up to its other end, that may possibly be expanded and disengaged from the balloon 4.

Meanwhile, the vascular stent 5, mounted on the balloon 4 of the catheter 2, is promptly expanded with expansion of the balloon 4, brought about by removal of the force of support by the protective sheath 1, caused by relative movement of the protective sheath 1 with respect to the catheter 2. Since the temporary holding member 23 is adapted for holding the outer peripheral surface 2a of the catheter 2 and the one end side of the vascular stent 5, as shown in FIG. 5, the temporary holding member 23 keeps on to hold the one end side of the vascular stent 5, in the initial stage of expansion of the balloon 4 for expanding the vascular stent 5. However, when the vascular stent 5 is expanded further, the temporary holding member 23 becomes detached from the vascular stent 5 and is left on the catheter 2. That is, the vascular stent 5 is disengaged from the temporary holding member 23, because the vascular stent 5 is expanded beyond the expansion yield point of the temporary holding member 23.

The vascular stent 5 may be freed more reliably from the retention by the temporary holding member 23 by setting the width of the part of the temporary holding member 23, lying on the outer peripheral surface 2a of the catheter 2, so as to be larger than the width of the part of the temporary holding member lying on the one end side of the vascular stent 5, or by bonding the temporary holding member to the outer peripheral surface of the catheter using an adhesive.

Since the temporary holding member 23 holds only the one end side of the vascular stent 5, the temporary holding member may readily be detached from the vascular stent 5, without obstructing the expansion of the vascular stent 5, when the vascular stent 5 is expanded with expansion of the balloon 4. Moreover, since the one end side of the vascular stent 5, lying towards the inner side of the protective sheath 1, is retained by the temporary holding member 23, the vascular stent 5, once protruded to outside the protective sheath 1, may subsequently be housed again within the protective sheath 1.

Figure 11:
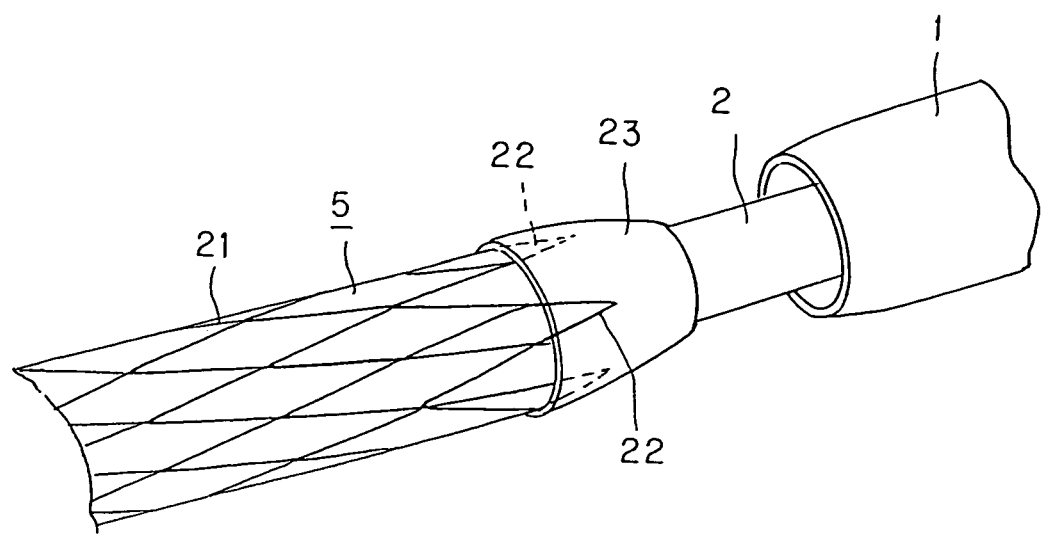
FIG. 11 is a side view showing another instance of the state in which the stent for a vessel, mounted on the catheter, is retained.

When the vascular stent 5, formed using the yarn 21 of the biodegradable polymer, is freed from support by the protective sheath 1, the temporary holding member 23 has to hold the vascular stent 5 in such a manner as to prevent the vascular stent 5 from being jumped up from the protective sheath 1, and in such a manner as not to obstruct the expansion of the stent by the balloon 4. Thus, it is sufficient for the temporary holding member 23 to hold a small region towards one end side of the vascular stent 5, as shown in FIGS. 8 and 9. It is also unnecessary for the temporary holding member 23 to hold the entire outer rim portion of the one end side of the vascular stent 5. In the case of the vascular stent 5, formed by bending the yarn 21 in a zigzag pattern to form a pattern of a concatenation of vee shapes and by spirally winding the resulting zigzag pattern of the yarn, as shown in FIG. 7, it is sufficient that part of plural vee-shaped parts 22 of a ring pattern is retained by one end of the temporary holding member, as shown in FIG. 11.

The catheter 2, mounting the vascular stent 5 on the balloon 4 as described above, is inserted from the proximal end of the protective sheath 1 into the inner bore opening 3, with the distal end carrying the vascular stent 5 first, as shown in FIGS. 1 and 2. By inserting the catheter 2 into the inner bore opening 3 of the protective sheath 1, the vascular stent 5, mounted on the distal end of the catheter 2, is also inserted into the inside of the protective sheath 1. The inner bore opening 3 for the catheter 2, provided in the protective sheath 1, is formed to an inner diameter approximately equal to the outer diameter of the part at the distal end of the catheter 2 carrying the balloon 4 and the vascular stent 5. The result is that the vascular stent 5, mounted on the catheter 2, is inserted into the inner bore opening 3 for the catheter 2 of the protective sheath 1, so as to be maintained in its contracted state.

Figure 12:
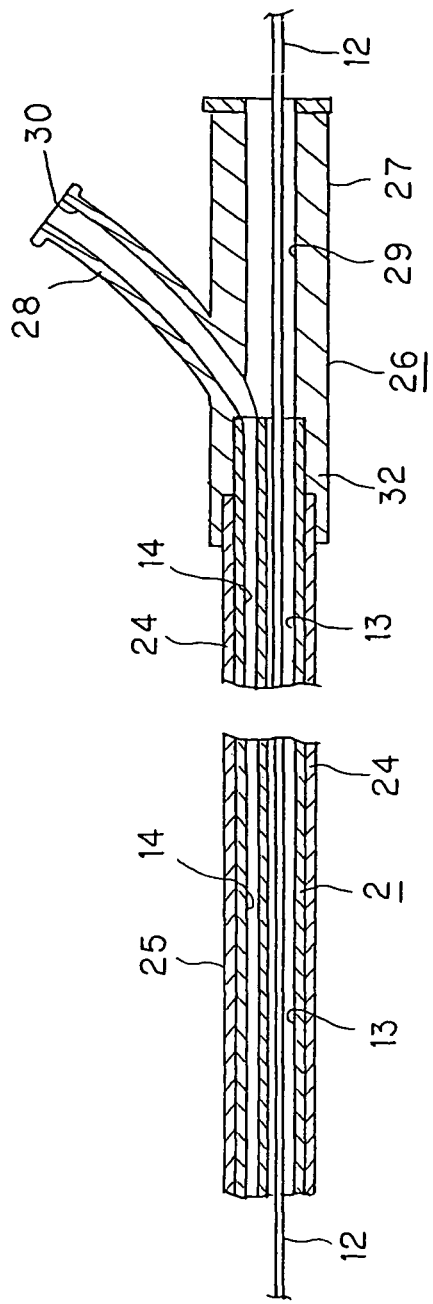
FIG. 12 is a cross-sectional view showing the proximal side end of the catheter provided with a bend control part for preventing the bending of the catheter.

The proximal end side of the catheter 2, opposite to its distal end side carrying the vascular stent 5, operates as a catheter reciprocation portion which is held by the operator's finger when the catheter 2 is protruded from the protective sheath 1 and reciprocated relative to the protective sheath 1, as shown in FIG. 1. This catheter reciprocation portion is provided with a bend control part 25 for preventing the bending of the catheter 2 formed as a long tube from a readily bendable synthetic polymer material, such as polyethylene polymer. The bend control part 25 is formed by providing a tube 24, formed of a highly rigid material, insusceptible to deformation or flexure, to the outer periphery of the catheter 2, as shown in FIG. 12. This tube 24 is formed of metal, such as aluminum or stainless steel.

It should be noted that the proximal end of the catheter 2 is slightly protruded from one end of the metal tube 24 of the bend control part 25, for connecting a first connection fixture 26, which will be explained subsequently.

This first connection fixture 26 is mounted to the proximal end side of the catheter 2 provided with the bend control part 25, as shown in FIGS. 1 and 12. The first connection fixture 26 is formed of a highly rigid synthetic polymer material scarcely susceptible to elastic deformation. The first connection fixture is made up by a guide section 27 for guiding a guide wire 12 being inserted into the inner bore opening 13 and by a connecting section 28 to which is connected a fluid supply fitting adapted for delivery of a fluid to the balloon 4 through the fluid passage 14. The first connection fixture 26 is generally in a Y-shape by having the connecting section 28 branched from the guide section 27, adapted for guiding the guide wire, as shown in FIG. 12.

The guide section 27 for guiding the guide wire, making up the first connection fixture 26, is provided with a first through-hole 29 communicating with the inner bore opening 13 for the guide wire of the catheter 2, whilst the connecting section 28 is provided with a second through-hole 30 communicating with the fluid passage 14 of the catheter 2. The first connection fixture 26 is provided to the proximal end part of the catheter 2, with the first through-hole 29 communicating with the inner bore opening 13 for the guide wire 2, and with the second through-hole 30 communicating with the fluid passage 14. That is, the first connection fixture 26 is provided in position, by fitting a tubular connector 32, provided on its one side, and which is made up by the guide section 27 and the connecting section 28, unified to each other, to the proximal end of the catheter 2. In this case, an end part of the tube 24, forming the bend control part 25 on the proximal end part of the catheter 2, is fitted to the tubular connector 32. In this manner, the proximal end side of the catheter 2 is protected against flexure or bending, by being provided with the bend control part 25, to which is connected the first connection fixture 26. This first connection fixture is formed of a tough synthetic polymer material, as is the bend control part 25

The catheter 2, formed as described above, is inserted into the inner bore opening 3 for the catheter 2 of the protective sheath 1, with its distal end side, provided with the balloon 4 and fitted with the vascular stent 5, as an inserting end side, as shown in FIGS. 1 and 2.

Meanwhile, the protective sheath 1 is used for the purpose of supporting the vascular stent 5, formed of a biodegradable polymer, and which has the properties of self-expanding on heating to the state expanded in diameter, in a contracted state. Thus, the inner bore opening 3 for the catheter 2, formed in the protective sheath 1, has a diameter (inner diameter) approximately equal to or slightly larger than the outer diameter of the vascular stent 5, mounted in a state contracted in diameter to the distal end of the catheter 2. When the catheter 2, formed to such size, is inserted into the inner bore opening 3 for the catheter 2, it may be feared that large frictional resistance is generated between the inner peripheral surface of the inner bore opening 3 for the catheter and the vascular stent 5 mounted to the catheter 2. However, since the protective sheath 1, used in the present invention, is provided on its inner peripheral surface with the inner coating layer 8, the catheter 2, mounting the vascular stent 5, may smoothly be inserted into the inside of the protective sheath 1, while the protective sheath 1 may smoothly be reciprocated relative to the catheter 2.

The vascular stent 5, inserted into the protective sheath 1, formed as described above, is kept inserted in the protective sheath 1, as shown in FIG. 2, so that it is kept in the state of being supported in a state contracted in diameter by the protective sheath 1.

The vascular stent 5, mounted on the catheter 2, is delivered as far as a targeted site for implantation in the blood vessel of the living body, and subsequently is protruded from within the protective sheath 1 so as to be expanded in diameter by expansion of the balloon 4. Thus, the catheter 2, mounting the vascular stent 5 thereon, and the protective sheath 1, may be reciprocated relative to each other at least between the position in which the vascular stent 5 is housed in the protective sheath 1 and the position in which the vascular stent 5 has been displaced to outside the protective sheath 1. Thus, if the catheter 2 is inserted into the blood vessel, along with the protective sheath 1, and the catheter 2 or the protective sheath 1 is moved, there is the risk that the vascular stent 5, mounted to the distal end of the catheter 2, is protruded from the distal end of the protective sheath 1. If the vascular stent 5, formed of the biodegradable polymer, is freed from support by the protective sheath 1, and is heated by body temperature of the living body, the vascular stent 5 is expanded from the contracted state to the state enlarged in diameter. The result is that the vascular stent 5 is detached from the balloon 4 provided on the catheter 2. Hence, it may be feared that not only the vascular stent ceases to be expandable by the balloon 4 but also it ceases to be deliverable to the targeted site for implantation in the blood vessel.

Thus, the protective sheath 1 and the catheter 2, inserted into the inside of the protective sheath 1, need to be secured to each other, in order to prevent the protective sheath or the catheter from being inadvertently moved back and forth in the course of delivery of the vascular stent 5 to a site for implantation in the blood vessel or during storage, so as not to cause the vascular stent to be protruded from the protective sheath 1.

In the inner bore opening 3 for the catheter of the protective sheath 1, into which is inserted the catheter 2, there is provided a spacing between the outer peripheral surface of the catheter 2 and the protective sheath 1, extending along the entire length of the protective sheath 1, as shown in FIG. 2. In this spacing is charged a liuid, such as physiological saline.

Figure 13:
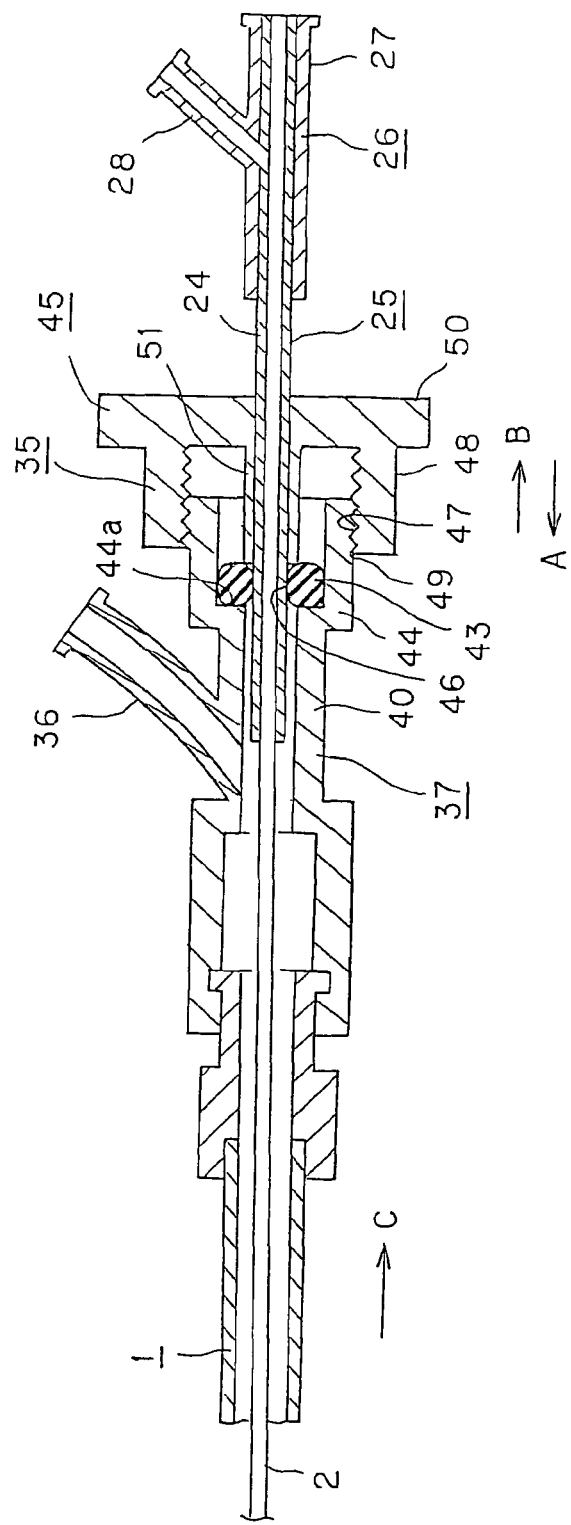
FIG. 13 is a cross-sectional view showing a second connection fixture provided with a fixation unit for fixing the catheter to a protective sheath.

Thus, the proximal end part of the protective sheath 1 is provided with a fixation unit 35, for preventing the catheter 2 inserted into the protective sheath 1, and the protective sheath 1, from performing relative movement to each other, and a second connection fixture 37 provided with a liquid supply fixture connecting part 36, fitted with a liquid charging fixture for charging the liquid, such as physiological saline, into the inner bore opening 3 for the catheter, as shown in FIGS. 1 and 13.

The proximal end of a catheter inserting part 40, forming the second connection fixture 37, is provided with the fixation unit 35 for securing the catheter 2 inserted into the catheter inserting part 40, as shown in FIG. 13. The fixation unit 35 includes a catheter tightening member 43 of an elastic material, such as rubber, inserted within the catheter inserting part 40, and through which is passed the catheter 2, a holder for the catheter tightening member 44 for holding the catheter tightening member 43 as it is housed therein, and a compressing fixture 45 for compressing the catheter tightening member 43 housed within the holder for the catheter tightening member 44, as shown in FIG. 13.

The catheter tightening member 43 is formed as a ring having a catheter inserting center opening 46 passed through by the catheter 2. The holder for the catheter tightening member 44 is formed as one with and at the proximal end of the catheter inserting part 40, in the manner of enhancing the diameter of the catheter inserting part 40. The catheter tightening member 43 is housed as it is set on a bottom 44a of the holder for the catheter tightening member 44. The compressing fixture 45 is mounted for performing reciprocating movement on the holder for the catheter tightening member 44 and is mounted by screwing a tubular fitting part 48 having a tapped portion 47 to the holder for the catheter tightening member 44 having a mating yarned portion 49 on its outer peripheral surface. The proximal end part of the tubular fitting part 48 is provided with a rotation part 50 for causing rotation of the compressing fixture 45. The compressing fixture 45 is provided with a center press-mounting part 51 for compressing the catheter tightening member 43 housed in the holder for the catheter tightening member 44 for press fitting the catheter tightening member against the catheter 2 inserted into the catheter tightening member 43. The press-mounting part 51 is formed as a tube arranged in a radially inner area of and coaxially as the fitting part 48. The catheter 2 is inserted through this press-mounting part 51. As the compressing fixture 45 is progressively screwed to the holder for the catheter tightening member 44, the press-mounting part 51 is intruded into the inside of the holder 44 to compress the catheter tightening member 43 housed within the holder for the catheter tightening member 44.

The catheter tightening member 43 is housed within the holder 44 so that the outer diameter of the outer peripheral part of the catheter tightening member will be suppressed from increasing on compression of the catheter tightening member. Thus, when thrust by the press-mounting part 51, the catheter tightening member 43 is compressed for reducing the diameter of the catheter inserting center opening 46 for pressure fitting the catheter tightening member against the catheter 2 inserted through the catheter inserting center opening 46. The catheter 2 has a press fit with the catheter tightening member 43 of the fixation unit 35 provided to the second connection fixture 37 mounted to the proximal end of the protective sheath 1, whereby the catheter 2 is prohibited from performing a reciprocating movement with respect to the protective sheath 1 to secure the position of insertion thereof in the protective sheath 1.

The inside of the holder for the catheter tightening member 44 is hermetically sealed by the press-fitting the catheter tightening member 43 to the catheter 2. By hermetically sealing the proximal end side of the second connection fixture 37, the liquid, such as physiological saline charged via liquid supply fitting mounted to the liquid supply fixture connecting part 36, provided to a mid part of the second connection fixture 37, is charged through a check valve 42 into the inner bore opening 3 for the catheter, without leaking out of the catheter inserting part 40, and further discharged via inner bore opening 3 for the catheter to outside the protective sheath 1.

When the compressing fixture 45 of the fixation unit 35 is rotated to cause the press-mounting part 51 to be receded from the catheter tightening member 43 to decompress the catheter tightening member 43, the catheter 2, whose position of insertion relative to the protective sheath 1 has been fixed, is freed of the tightening by the catheter tightening member 43 and hence is able to perform relative movement with respect to the protective sheath 1.

Meanwhile, the bend control part 25, provided to the proximal end side of the catheter 2, is of such a length that the bend control part remains within the inside of the fixation unit 35, provided to the proximal end side of the second connection fixture 37, when the vascular stent 5, mounted to the distal end of the catheter 2, is moved from the position in which the stent is housed within the protective sheath 1 as far as the position in which it is protruded from the protective sheath 1. The catheter 2, inclusive of the bend control part 25 of a highly rigid material, and the second connection fixture 37, mainly composed of a rigid synthetic polymer material, and into which is inserted the bend control part 25, is free from flexural deformation and hence may be moved back and forth, as its linear state is maintained, thus assuring stabilized reciprocating movement of the catheter 2.

The state in which the vascular stent 5 is implanted in the blood vessel of the living body, using the above-described stent delivery system of the present invention, will now be explained.

First, for implanting the vascular stent 5 in the blood vessel, the vascular stent 5, mounted in a state contracted in diameter on the balloon 4, similarly contracted in diameter, is placed and housed in the protective sheath 1, as shown in FIG. 2. That is, the catheter 2 is fixed as the vascular stent 5, mounted to its distal end side, is housed within the protective sheath 1. The catheter 2 is secured to the protective sheath 1 by screwing the compressing fixture 45 to the holder 44 in a direction indicated by an arrow A in FIG. 13 to compress the catheter tightening member 43 by the press-mounting part 51.

The inner bore opening 3 for the catheter of the protective sheath 1 is then degassed by charging the physiological saline into the inner bore opening 3 for the catheter from a drug inlet fixture connected to the liquid supply fixture connecting part 36 provided to the second connection fixture 37. The physiological saline, charged from the drug inlet fixture, is charged into the inner bore opening 3 for the catheter.

After degassing the inner bore opening 3 for the catheter, the protective sheath 1 and the catheter 2 are inserted into the blood vessel of the living body, with the distal end side of the protective sheath 1 as an inserting end. The flexible guide wire 12 of a fine diameter, inserted into the inner bore opening 13 for the guide wire of the catheter 2, is inserted into the blood vessel ahead of the protective sheath 1 and the catheter 2. The protective sheath 1 and the catheter 2 are inserted into the blood vessel with the guide wire 12 as guide. Since the flexible insertion protecting part 10 is provided to the distal end of the protective sheath, the protective sheath and the catheter 2 may be inserted such as to protect the inner wall of the blood vessel.

The protective sheath 1 and the catheter 2 are inserted into the blood vessel until the vascular stent 5, housed in the protective sheath 1, reaches the site for implantation in the blood vessel.

The position of insertion of the protective sheath 1 into the blood vessel may be confirmed from outside the living body using the radiopaque section 11 mounted to its distal end. The position of insertion into the blood vessel of the vascular stent 5, housed in the protective sheath 1, may be confirmed from outside the living body using the radiopaque sections 16, 17 provided to the balloon 4 carrying the vascular stent 5. In case the vascular stent 5, provided with the radiopaque section, is used, the inserting position may be confirmed from outside the living body using the radiopaque section provided to the vascular stent 5. If in particular the radiopaque sections are provided to both the balloon 4 and the vascular stent 5, not only the inserting position in the blood vessel of the vascular stent 5, but also the relative position between the balloon 4 and the vascular stent 5 may be confirmed and hence it may be correctly determined whether or not the vascular stent 5 has been mounted in position on the balloon 4, with the result that the vascular stent 5 may reliably be expanded in diameter, using the balloon 4.

Furthermore, by confirming the positions of the radiopaque section 11 provided to the protective sheath 1 and the radiopaque section provided to the balloon 4 or to the vascular stent 5, it is possible to determine the position of the vascular stent 5 relative to the protective sheath 1.

After introducing the protective sheath 1 and the catheter 2 until the vascular stent 5 has reached the site for implantation in the blood vessel, the compressing fixture 45 of the fixation unit 35 provided to the second connection fixture 37 is rotated to cause movement of the compressing fixture in a direction indicated by arrow B in FIG. 13 to release the compression of the catheter tightening member 43 by the press-mounting part 51 to release the fixation of the catheter 2 against the protective sheath 1 by the catheter tightening member 43.

The protective sheath 1 and the catheter 2, freed of tightening by the catheter tightening member 43, may now be reciprocated relative to each other. As the bend control part 25, provided to the proximal end side of the catheter 2, is gripped, the protective sheath 1 is moved relative to the catheter 2 in the direction indicated by arrow C in FIG. 13. When the protective sheath 1 is moved along the direction of arrow C in FIG. 13, the distal end of the catheter 2 is protruded from the distal end of the protective sheath 1, so that the vascular stent 5, mounted on the balloon 4, is protruded along with the balloon 4 to outside the protective sheath 1, as shown in FIG. 9.

The vascular stent 5, protruded from the protective sheath 1, may be adjusted as to its site for implantation in the blood vessel by reciprocating the catheter 2 as necessary.

Meanwhile, the vascular stent 5, used in the present invention, is warmed by body temperature, as the vascular stent, housed in the protective sheath 1, is transported within the blood vessel of the living body, such that a force of expansion is accumulated in the vascular stent 5 which will set the vascular stent 5 from its contracted state to its state expanded in diameter.

When the vascular stent 5, in which the force of expansion has been accumulated as described above, is protruded from the protective sheath 1, the vascular stent is freed of the support by the protective sheath 1, and hence is expanded in the direction of expanding its diameter.

In the stent delivery system according to the present invention, the vascular stent 5, mounted on the balloon 4, provided to the catheter 2, has its one end towards the inner side of the protective sheath 1 carried by the temporary holding member 23, so that, when the vascular stent is protruded from the protective sheath 1, the opposite side end of the stent, protruded first from the distal end of the protective sheath 1, is expanded in diameter, while the one end side thereof remains mounted on the balloon 4 and is in a state contracted in diameter, as shown in FIG. 9. That is, the vascular stent 5 has its one end side carried by the temporary holding member 23, so that, even if the stent is protruded from the protective sheath 1, it is not separated from the balloon 4 and is maintained at a certain relative position with respect to the balloon 4. Consequently, the vascular stent 5 may reliably be kept in the state enlarged in diameter by the expansion of the balloon 4.

The catheter 2, which has caused the vascular stent 5 to be protruded from the protective sheath 1 and has performed the back-and-forth movement to set the vascular stent at a targeted site for implantation in the blood vessel, is secured to the protective sheath 1. This securing of the catheter 2 to the protective sheath 1 is carried out by compressing the catheter tightening member 43 of the fixation unit 35, as described above.

After securing the catheter 2 to the protective sheath 1, the balloon 4 is expanded by charging a liquid, such as contrast agent, supplied to the fluid passage 14 of the catheter 2, into the balloon 4 via through-hole 15. The contrast agent, adapted for expanding the balloon 4, is supplied to the fluid passage 14 from a balloon expanding/contracting fixture, connected to the connecting section 28, provided to the first connection fixture 26, and is thence charged via through-hole 15 into the inside of the balloon 4.

Figure 14:
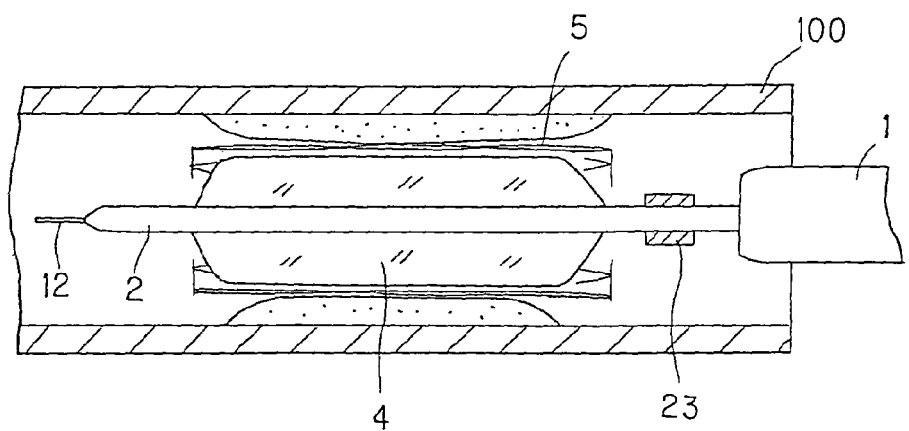
FIG. 14 is a cross-sectional view showing the state in which the stent for a vessel is inserted into the blood vessel of a living body and the balloon is expanded to dilate the stent in diameter.

When the balloon 4 is expanded, the vascular stent 5, mounted to the outer peripheral side of the balloon 4, is expanded with the expansion of the balloon 4, as shown in FIG. 14. Before and at an earlier stage of expansion of the balloon 4, the opposite end side of the vascular stent 5, not retained by the temporary holding member 23, has been expanded to its state enlarged in diameter, as shown in FIG. 9. However, the one end side of the vascular stent 5 is held in its contracted state by the temporary holding member 23. Consequently, the vascular stent 5 is enlarged in diameter with expansion of the balloon 4. The vascular stent 5, expanded in diameter with the expansion of the balloon 4, is implanted in a lesion of hyperplasia, which has caused the stenosis in the blood vessel 100, to support the wall of the blood vessel from the inside, as shown in FIG. 14.

Figure 15:
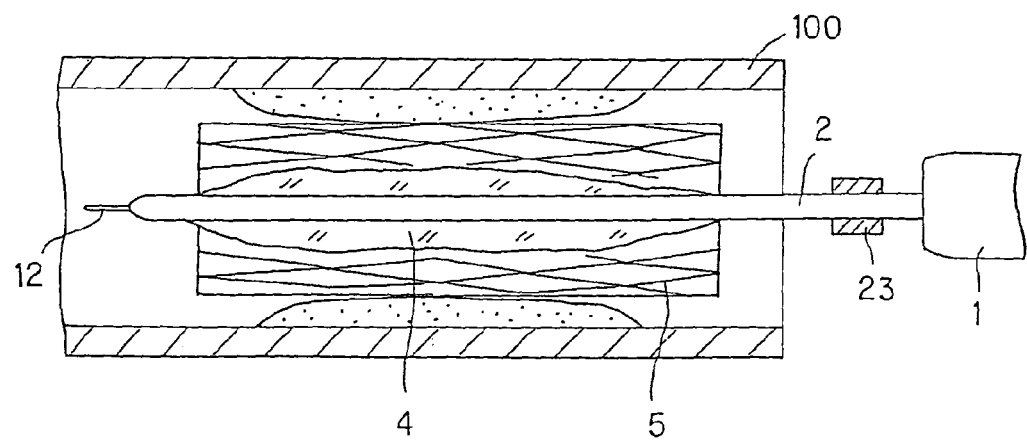
FIG. 15 is a cross-sectional view showing the state in which the stent for a vessel is inserted into the blood vessel of the living body and expanded in diameter and subsequently the balloon is contracted.

The balloon 4, expanded for expanding the diameter of the vascular stent 5, is contracted after expanding the vascular stent 5 in diameter, as shown in FIG. 15. The balloon 4 thus expanded is contracted by the balloon expanding/contracting fixture sucking up the contrast agent charged into the balloon 4.

Since the vascular stent 5, used for the present invention, has the self-expanding function, the force of expansion which tends to keep the state of diameter expansion as at the time of the preparation acts after contraction of the balloon 4, and hence the blood vessel 100 is expanded from its inside, as shown in FIG. 15.

After the vascular stent 5, mounted on the catheter 2, is expanded and implanted in the site of stenosis in the blood 100, the protective sheath 1 and the catheter 2 are extracted from within the vessel.

As described above, with the protective sheath 1 and the catheter 2 thus extracted from within the blood vessel 100, the vascular stent 5 is ultimately implanted within the blood vessel 100.

It should be noted that, with the protective sheath 1, used for the delivery system for the vessel, according to the present invention, the flexible tubular part 9, superior in flexibility to the proximal end side, is provided to the distal end side, and hence the protective sheath 1 may readily be inserted into the curved or sinuous blood vessel, so as to conform to the shape of the blood vessel. Since the flexible tubular part 9 is curved to conform to the shape of the blood vessel, in which the protective sheath 1 is to be inserted, the flexible tubular part 9 may be smoothly inserted without applying a large load on the aorta curved to a U-shape. Consequently, the vascular stent 5, mounted on the catheter 2, inserted into the protective sheath 1, may reliably and readily be implanted on the targeted site for implantation in the intricately bent or sinuous blood vessel.

In the foregoing explanation, the temporary holding member 23 for holding the vascular stent 5 contracted in diameter is formed using an elastic material, such as latex. However, the stent delivery system according to the present invention is not limited to using the temporary holding member of the above-described embodiment.

That is, such a temporary holding member, adapted for releasing the holding so as not to obstruct the expansion of the stent for a vessel with the expansion of the balloon, may be used. For example, such a temporary holding member may be used which is ruptured with the expansion of the balloon to release the holding of the vascular stent.

An instance of a stent delivery system, employing a temporary holding member ruptured with the expansion of the balloon, will now be explained with reference to the drawings.

The parts or components which are common to those of the above-described stent delivery system are depicted by the common reference numerals, and the detailed description is dispensed with.

Figure 16:
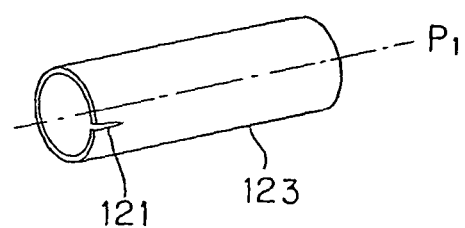
FIG. 16 is a perspective view showing a temporary holding member used for the stent delivery system according to another embodiment of the present invention.

A temporary holding member 123, used for the stent delivery system of the present embodiment, is formed to a tubular shape from a synthetic polymer material, as shown in FIG. 16. The synthetic polymer material of the temporary holding member 123 is a material not readily elastically deformed, such as latex, and may, for example, be PTFE (polytetrafluoroethylene).

Figure 17:
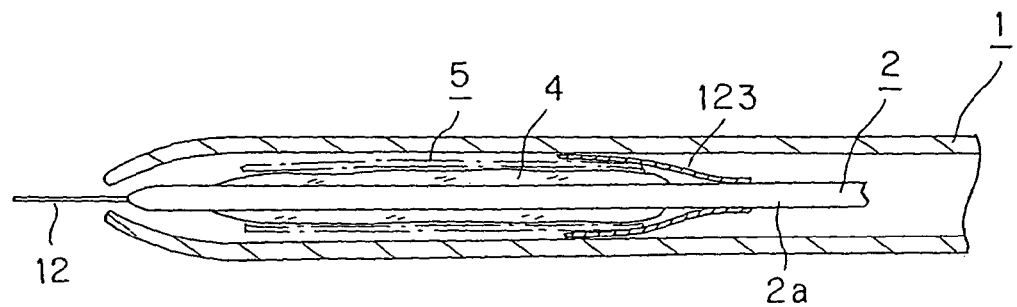
FIG. 17 is a cross-sectional view showing essential portions of the stent supplying device according to a further embodiment of the present invention.

The temporary holding member 123, formed of PTFE to a tubular shape, is drawn along the longitudinal direction $P_1$ of the tube axis. This temporary holding member 123 is loaded so as to cover up a region extending from one end side of the vascular stent 5, mounted on the balloon 4, as far as the outer peripheral area 2a of the catheter 2, as shown in FIG. 17. In one end towards the vascular stent 5 of the temporary holding member 123, there is formed a readily rupturable part 121 for guiding the cleavage of the temporary holding member 123. This rupturable part 121 is formed by forming a slit from one end of the temporary holding member 123 along the axial direction. The temporary holding member 123, provided with the rupturable part 121, and drawn axially, may readily be ruptured, with the rupturable part 121 as a guide for rupturing, when the balloon 4 is expanded and subjected to the diameter expanding force.

The opposite end side of the temporary holding member 123, lying on the outer peripheral surface 2a of the catheter 2, is bonded with an adhesive, or set fixedly using a yarn. Since the opposite side end of the temporary holding member 123 is secured to the catheter 2, the temporary holding member 123 may be prevented from becoming disengaged from the catheter 2 even in case the temporary holding member is ruptured along the rupturable part 121.

With the stent delivery system, the vascular stent 5 has its end side retained by the temporary holding member 123, so that, even in case the vascular stent is protruded from the protective sheath 1, it is possible, as in the above-described stent delivery system, to prevent the entire portions of the vascular stent 5 from the one end side up to the opposite end side, from being expanded and detached from the balloon 4.

Figure 18:
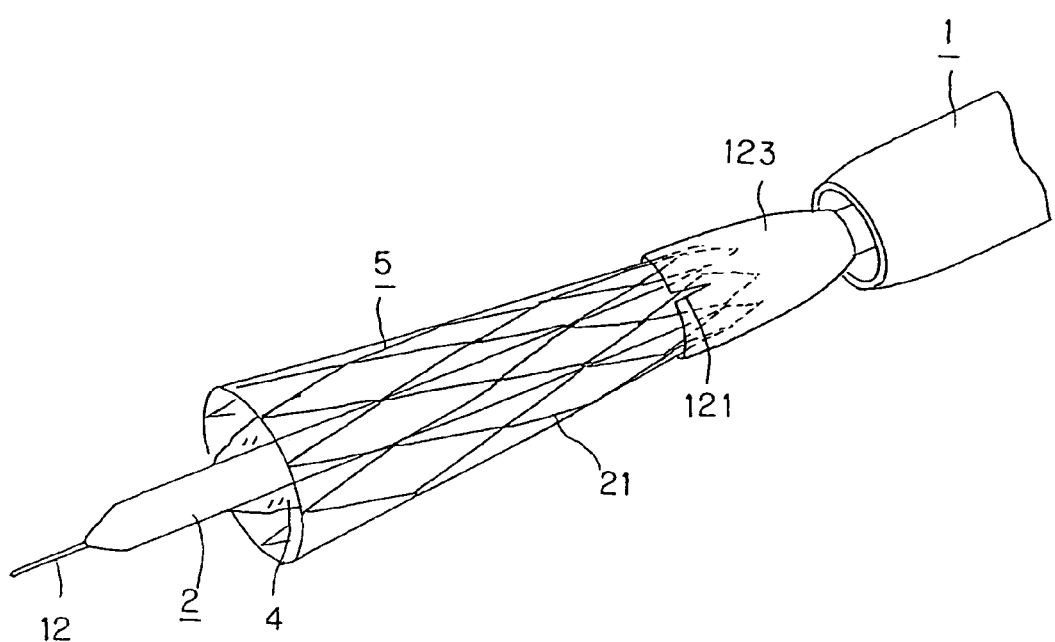
FIG. 18 is a perspective view showing a state of balloon expansion in a stent delivery system according to the present invention.

Meanwhile, with the stent delivery system of the present embodiment, when the catheter 2 is moved back and forth relative to the protective sheath 1, the vascular stent 5 is protruded, along with the balloon 4, to outside the protective sheath 1, and the balloon 4 is expanded, the force of expanding the diameter of the temporary holding member is applied from the balloon 4 to the temporary holding member 123. When the force of expanding the diameter, applied to the temporary holding member 123, exceeds the limit of expansion, the temporary holding member is ruptured with the rupturable part 121 as the guide for rupturing, as shown in FIG. 18. Since the temporary holding member 123 is drawn along the longitudinal direction $P_1$ of the tube axis, and is formed with the rupturable part 121 extending along the drawing direction, it may be ruptured readily along the axial direction.

The temporary holding member 123 is ruptured along the rupturable part 121 to release the retention of the vascular stent 5. The vascular stent 5, released from the holding by the temporary holding member 123, is expanded to conform to the expansion of the balloon 4.

With the stent delivery system of the present embodiment, the vascular stent 5, the force of self-expansion is imparted to, may reliably be retained by the balloon 4, thus assuring reliable retention with use of the balloon 4.

In the foregoing, an instance of employing a vascular stent, implanted in the blood vessel of the living body, has been explained. However, the present invention is not limited to the vascular stent and may extensively be used for stents for the vessel caused to remain in vessels, such as trachea, bile duct or urethra of the living body, to support the lumen of the vessel from the inside.

The present invention is not limited to the above-described embodiments explained with reference to the drawings and, as will be apparent to those skilled in the art, various changes, substitutions or equivalents may be attempted without departing from the scope of the invention as defined in the claims.

Industrial Applicability

With the stent delivery system, according to the present invention, described above, the vascular stent, which is formed of a biodegradable polymer and given the self-expanding properties, but which needs expansion using the balloon, may reliably be implanted on a targeted site for implantation in the vessel. Moreover, the vascular stent may be inserted in safety such as to suppress the damage to the vessel, such as blood vessel.

The invention claimed is:

1. A stent delivery system comprising:
   a protective sheath defining a distal end having a distal end diameter;
   a catheter inserted into said protective sheath for performing a back-and-forth movement therein;
   a balloon arranged on an outer peripheral surface towards a distal end of said catheter protruded from the distal end of said protective sheath, said balloon being expanded with a fluid supplied to said catheter;
   a stent formed of a biodegradable polymer to a tubular shape and mounted in a state having a contracted diameter on said balloon and being moved back and forth along with said balloon relative to said protective sheath, the contracted diameter being greater than the distal end diameter of the protective sheath; and
   a temporary holding member housed within the protective sheath which holds, at one end, the outer peripheral surface of the catheter and, at an opposite end, a proximal side end of the stent located opposite to the distal end of the protective sheath, operating as an end for protrusion,
   wherein the temporary holding member covers an outer surface of a single end of the stent such that it does not completely enclose the stent,
   wherein the proximal end of the stent is retained in a contracted state by the temporary holding member during initial expansion of the stent by expansion of the balloon but is released from the temporary holding member when the expansion of the stent exceeds an expansion limit of the temporary holding member, and
   wherein a distal side end of the stent located opposite to the proximal side end of the stent is retained only by the protective sheath such that when the stent is initially protruded from the protective sheath, the distal side end of the stent is expanded in diameter while the proximal side end is simultaneously retained in a contracted state by the temporary holding member.

2. The stent delivery system as defined in claim 1 wherein said temporary holding member is formed of an elastic material to a tubular shape.

3. The stent delivery system as defined in claim 2 wherein the end of the temporary holding member which holds the outer peripheral surface of the catheter is bonded to said catheter.

4. The stent delivery system as defined in claim 1 wherein said temporary holding member is formed of a synthetic polymer material to a tubular shape, said temporary holding member being drawn along the longitudinal direction of the tube axis, and being formed on one end side thereof with a readily rupturable part for guiding the rupturing accompanying the expansion of said balloon.

5. The stent delivery system as defined in claim 4 wherein said temporary holding member is formed of PTFE (polytetrafluoroethylene).

6. The stent delivery system as defined in claim 1 wherein a self-expanding function is imparted to said stent for a vessel.

7. The stent delivery system as defined in claim 1 wherein said stent for a vessel is formed of biodegradable polymer to a tubular shape and is afforded with a self-expanding function.

8. The stent delivery system as defined in claim 1 wherein said stent for a vessel is formed from a yarn of a biodegradable polymer to a tubular structure, and provided with a self-expanding function, said stent for a vessel being wound to a tube as the yarn is bent in a zigzag design, and expanded or contracted in diameter with the bends of the yarn as displacing portions.

9. The stent delivery system as defined in claim 1 wherein said protective sheath is formed of a material suppressed from performing extension/contraction along the direction of the longitudinal axis thereof.

10. The stent delivery system as defined in claim 1 wherein said protective sheath has a portion thereof towards a side for insertion into a vessel of a living body curved to conform to the shape of said vessel.

11. The stent delivery system as defined in claim 1 wherein said protective sheath includes on the distal side for insertion into said vessel a flexible tubular section superior in flexibility to the proximal end side thereof.

12. The stent delivery system as defined in claim 1 wherein said protective sheath includes on the distal side for insertion into said vessel an insertion protecting part exhibiting superior flexibility.

13. The stent delivery system as defined in claim 1 wherein said protective sheath includes a radiopaque section containing a radiopaque material on the distal end side thereof from which is protruded said stent for a vessel mounted on said catheter.

14. The stent delivery system as defined in claim 1 wherein said catheter includes a radiopaque section indicating the mounting position of said stent for a vessel.

15. The stent delivery system as defined in claim 1 wherein said protective sheath includes a radiopaque section containing a radiopaque material on the distal end side hereof from which is protruded said stent for a vessel mounted on said catheter and wherein said catheter inserted into said protective sheath includes a radiopaque section indicating the mounting position of said stent for a vessel.

16. The stent delivery system as defined in claim 1 wherein the proximal side of the stent includes a plurality of vee-shaped portions, and only the vee-shaped portions of the stent are held by the temporary holding member.

17. The stent delivery system as defined in claim 1 wherein the temporary holding member includes a readily rupturable part for facilitating the rupture of the temporary holding member from the stent.

18. The stent delivery system as defined in claim 17 wherein the readily rupturable part is a slit beginning at one end of the temporary holding member and extending along the axial direction of the temporary holding member.

19. The stent delivery system as defined in claim 1 wherein a proximal end of the protective sheath located opposite to the distal end of the protective sheath is provided with a fixation unit that prevents the catheter from performing relative movement with respect to the protective sheath.

20. The stent delivery system as defined in claim 1 wherein the temporary holding member prevents expansion in diameter of the stent.

\* \* \* \* \*